(12) United States Patent
Peng et al.

(10) Patent No.: US 10,702,245 B2
(45) Date of Patent: Jul. 7, 2020

(54) METHOD OF DETECTING MICROBUBBLES IN A VESSEL

(71) Applicant: National Tsing Hua University, Hsinchu (TW)

(72) Inventors: Hsu-Hsia Peng, Hsinchu (TW); Che-Wei Wu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 300 days.

(21) Appl. No.: 15/586,879

(22) Filed: May 4, 2017

(65) Prior Publication Data
US 2018/0317886 A1 Nov. 8, 2018

(51) Int. Cl.
| | |
|---|---|
| *A61B 8/08* | (2006.01) |
| *A61B 5/055* | (2006.01) |
| *A61B 8/06* | (2006.01) |
| *G01R 33/563* | (2006.01) |
| *G01R 33/48* | (2006.01) |
| *G06T 7/00* | (2017.01) |
| *A61K 9/50* | (2006.01) |
| *A61B 8/00* | (2006.01) |
| *A61K 49/18* | (2006.01) |

(52) U.S. Cl.
CPC ............. *A61B 8/481* (2013.01); *A61B 5/055* (2013.01); *A61B 8/06* (2013.01); *A61B 8/4416* (2013.01); *A61K 9/5015* (2013.01); *A61K 49/1809* (2013.01); *G01R 33/4814* (2013.01); *G01R 33/56316* (2013.01); *G06T 7/0012* (2013.01); *A61B 8/587* (2013.01); *G06T 2207/10088* (2013.01); *G06T 2207/30104* (2013.01)

(58) Field of Classification Search
CPC . A61B 8/481; A61B 8/06; A61B 5/055–0555; G01R 33/56316; G01R 33/20–64; G01S 7/52039
See application file for complete search history.

(56) References Cited

U.S. PATENT DOCUMENTS

| | | | | |
|---|---|---|---|---|
| 2009/0117177 | A1* | 5/2009 | Rapoport | A61K 9/1075 424/450 |
| 2010/0022887 | A1* | 1/2010 | Main | A61B 8/06 600/454 |
| 2015/0360020 | A1* | 12/2015 | Wu | G01R 33/4814 600/411 |

OTHER PUBLICATIONS

H.Y. Yu et al. "Quantification of the Pulse Wave Velocity of the Descending Aorta Using Axial Velocity Profiles From Phase-Contrast Magnetic Resonance Imaging". Magnetic Resonance in Medicine 56:876-883 (2006) (Year: 2006).*
P. Dayton et al. "Acoustic Radiation Force In Vivo: A Mechanism to Assist Targeting of Microbubbles". Ultrasound in Med. & Biol., vol. 25, No. 8, pp. 1195-1201, 1999 (Year: 1999).*

(Continued)

*Primary Examiner* — Jeffrey G Hoekstra
*Assistant Examiner* — Milton Truong
(74) *Attorney, Agent, or Firm* — WPAT, PC

(57) ABSTRACT

The present invention provides a method of detecting microbubbles in a vessel of an affected part, comprising aggregates the microbubbles, acquiring phase-contrast magnetic resonance images and analyzing the phase-contrast magnetic resonance images. Thus, we can detect or monitor the size and location of the microbubbles in vessels of any part of body.

12 Claims, 9 Drawing Sheets
(2 of 9 Drawing Sheet(s) Filed in Color)

(56) References Cited

OTHER PUBLICATIONS

K. K. Wong et al. "Cardiac Flow Analysis Applied to Phase Contrast Magnetic Resonance Imaging of the Heart". Annals of Biomedical Engineering, vol. 37, No. 8, Aug. 2009 (Year: 2009).*
P. Dyverfeldt "Quantification of Intravoxel Velocity Standard Deviation and Turbulence Intensity by Generalizing Phase-Contrast MRI". Magnetic Resonance in Medicine 56:850-858 (2006) (Year: 2006).*
Von Spiczak J, Crelier G, Giese D, Kozerke S, Maintz D, Bunck AC (2015) Quantitative Analysis of Vortical Blood Flow in the Thoracic Aorta Using 4D Phase Contrast MRI. PLoS One 10(9): e0139025. (Year: 2015).*
Zhe-Wei Wu et al., Assessments of flow velocity changes by phase-contrast MRI near acoustic radiation force aggregated bubbles, SMRT 25th annual meeting, May 7-13 2016, pp. 1-3, Singapore.
Che-Wei Wu et al., Quantification of acoustic radiation force induced flow velocity changes by phase-contrast MRI, ISMRM 25th annual meeting, Apr. 22-27, 2017, pp. 1-3 and pp. 1-14, Honolulu, HI.
Che-Wei Wu et al., Quantification of temporal standard deviation of flow velocity to access flow near acoustic radiation force aggregated bubbles by phase-contrast MRI.

* cited by examiner

METHOD OF DETECTING MICROBUBBLES IN A VESSEL

BACKGROUND OF THE INVENTION

1. Field of the Invention

The present invention relates to a method of detecting microbubbles in a vessel of an affected part. More specifically, the present invention relates to a method of detecting microbubbles in a vessel of an affected part using acoustic radiation force and phase-contrast magnetic resonance imaging (PC-MRI) techniques.

2. The Prior Arts

The use of microbubbles (MBs) in echocardiography was first reported in 1968. MBs are highly echogenic in vivo due to the mismatch in acoustic impedance between their gas cores and surrounding tissues. Intravenous injection (IV) administered MBs are capable of increasing the intensity of backscattered ultrasound by up to 20-30 dB, therefore serving as excellent ultrasound imaging contrast agents. In addition to their contrast-enhancing ability for diagnostic applications, MBs also possess unique properties for therapeutic applications. Recently, the use of MBs in conjunction with non-thermal pulsed-mode ultrasound has been investigated to enhance blood-tissue drug permeability for therapeutic applications.

The concept of therapeutic agents being encapsulated in or conjugated with MBs has been developed over the past few years. In addition to the synergistic effects of ultrasound and MBs to enhance the permeability of biological barriers such as cell membranes, small blood vessels, and the blood-brain barrier (BBB), as discussed above, MBs can serve as protective drug carriers. Another advantage is that the encapsulated agents can be released during the ultrasound-triggered MB destruction process. Chemotherapeutic drugs can thus be directly and specifically delivered to target tissues via ultrasound-mediated perforations, whereas the uptake of the drugs by non-target tissues is reduced. The encapsulated agents are conjugated close to the shell of MBs, increasing the opportunity for microstreams, shock waves, and microjets to drive them toward the tissues and enhance their uptake in the ultrasound-treated region.

Several strategies have been proposed for incorporating therapeutic agents in MB carriers, including attachment to the outer shell surface, embedding within the shell, dissolving hydrophobic drugs in the oily layer between the gas core and shell, and linking them to the shell.

Since MBs act as ultrasound contrast agents, the drug delivery process can also be concurrently monitored by detecting the drug-loaded MBs. However, the sonographic devices have trouble penetrating bone. For example, sonography of the adult brain is very limited. Therefore, monitoring the MBs in a body part enclosed by bone structure is still difficult.

SUMMARY OF THE INVENTION

The primary purpose of the present invention is to provide a method of detecting microbubbles in a vessel of an affected part, comprising: delivering an ultrasonic energy within the affected part to aggregate the microbubbles to form a plurality of aggregated microbubbles; acquiring a phase-contrast magnetic resonance image by a magnetic resonance device; and analyzing the phase-contrast magnetic resonance image to obtain a velocity value of each pixel of a region of interest in the phase-contrast magnetic resonance image, wherein the plurality of aggregated microbubbles is located at a pixel that the velocity value is within the lowest 10%.

In an embodiment of the present invention, further comprising: analyzing the phase-contrast magnetic resonance image to obtain a vorticity value of each pixel of the region of interest; wherein the plurality of aggregated microbubbles is located at a pixel that the velocity value is within the lowest 10% and the vorticity value is −0.18 to 0.18.

In an embodiment of the present invention, the region of interest is an area of the vessel.

In an embodiment of the present invention, the microbubbles have a diameter of 1-1.5 μm and were substantially composed of $C_3F_8$ gas or $C_5F_{12}$ droplet core encapsulated by a lipid shell.

In the preferred embodiments of the present invention, the microbubbles further comprise drugs for treating the affected part.

In an embodiment of the present invention, the ultrasonic energy has a frequency of 0.83-1.25 MHz and an acoustic pressure of 0.025-0.1 MPa.

In an embodiment of the present invention, the phase-contrast magnetic resonance image is a plurality of phase-contrast magnetic resonance images in a time sequence.

In an embodiment of the present invention, the method described above further comprising: calculating a velocity change of each pixel of the region of interest in the plurality of phase-contrast magnetic resonance images, the velocity change is defined as follows:

$$\text{Velocity change } (\%) = \frac{\text{velocity} - \text{average velocity during } preFUS}{\text{average velocity during } preFUS} \times 100\%$$

wherein preFUS is a time duration before the ultrasonic energy delivered, and a concentration of the microbubbles is equal to (the velocity change−A)/B, wherein A is 1 to 1.5 and B is 7.56 to 11.34.

In an embodiment of the present invention, A is 1.25 and B is 9.45.

In an embodiment of the present invention, the method described above further comprising: calculating a temporal velocity standard deviation of each pixel of the region of interest in the plurality of phase-contrast magnetic resonance images; wherein a concentration of the microbubbles is equal to the temporal velocity standard deviation/C, and C is 0.04 to 0.06.

In an embodiment of the present invention, C is 0.05.

In an embodiment of the present invention, the method described above further comprising: calculating a temporal velocity standard deviation of each pixel of the region of interest in the plurality of phase-contrast magnetic resonance images; calculating a range of temporal velocity standard deviation which is 90th percentile of the temporal velocity standard deviation minus 10th percentile of temporal velocity standard deviation, wherein a concentration of the microbubbles is equal to (the range of the temporal velocity standard deviation−D)/E, and D is 0.0136 to 0.0204 and E is 0.0856 to 0.1284.

In an embodiment of the present invention, D is 0.017 and E is 0.107.

By the technical features above, we can use PC-MRI and ultrasonic energy to detect or monitor the size, location and concentration of MBs. Therefore, we can detect or monitor the drug dose near a target location by evaluate the size, location and concentration of drug-loaded MBs, even though the target location is enclosed by bone structure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

Unless otherwise defined, all technical and scientific terms used herein have the same meaning as commonly understood by one of ordinary skill in the art to which this invention pertains. In the case of conflict, the present document, including definitions will control.

As used herein, "approximately" shall generally mean within 20 percent, preferably within 10 percent, and more preferably within 5 percent of a given value or range. Numerical quantities given herein are approximate, meaning that the term "approximately" can be inferred if not expressly stated.

Figure 1A:
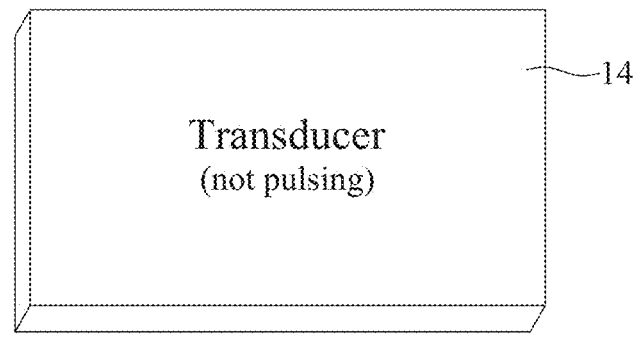
FIG. 1a is a schematic diagram showing MBs distributes in a vessel fulfilled with flowing fluid.
Figure 1A:
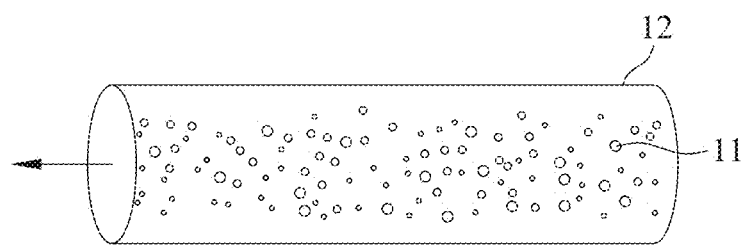
Figure 1B:
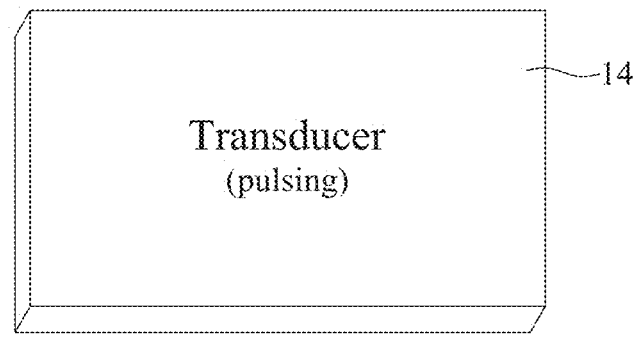
FIG. 1b is a schematic diagram shows MBs aggregated while applied focused ultrasound pulses by an ultrasound transducer.
Figure 1B:
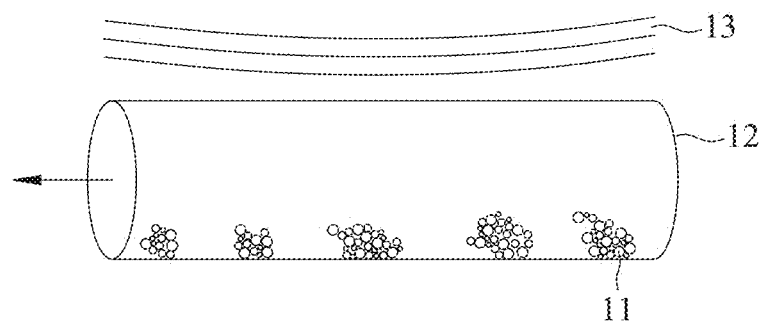

The primary radiation force and secondary radiation force can propel MBs to the wall of chamber or vessels and aggregate MBs to form a large-size bubble, respectively. FIG. 1a is a schematic diagram showing MBs 11 distributes in a vessel 12 fulfilled with flowing fluid. While we transmit focused ultrasound pulses 13, the MBs 11 are aggregated by secondary radiation force as shown in FIG. 1b. We base on these phenomenon and employ magnetic resonance imaging technique, which is not limited in bone shielding area imaging, to solve the problems described above.

Figure 2A:
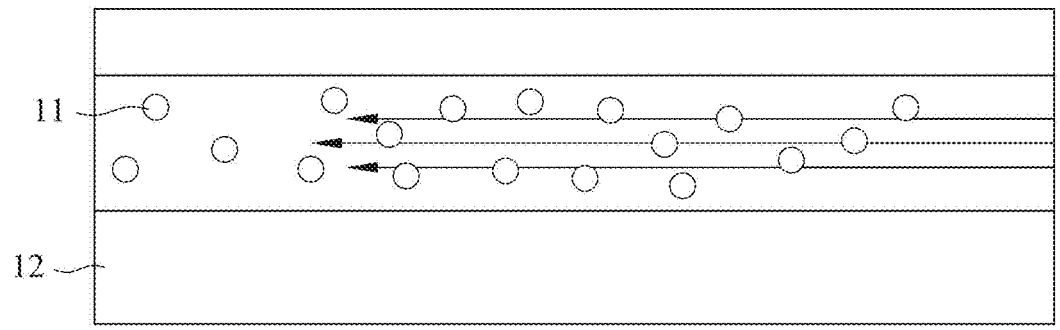
FIG. 2a is a schematic diagram showing flowing MBs in blood vessels.
Figure 2B:
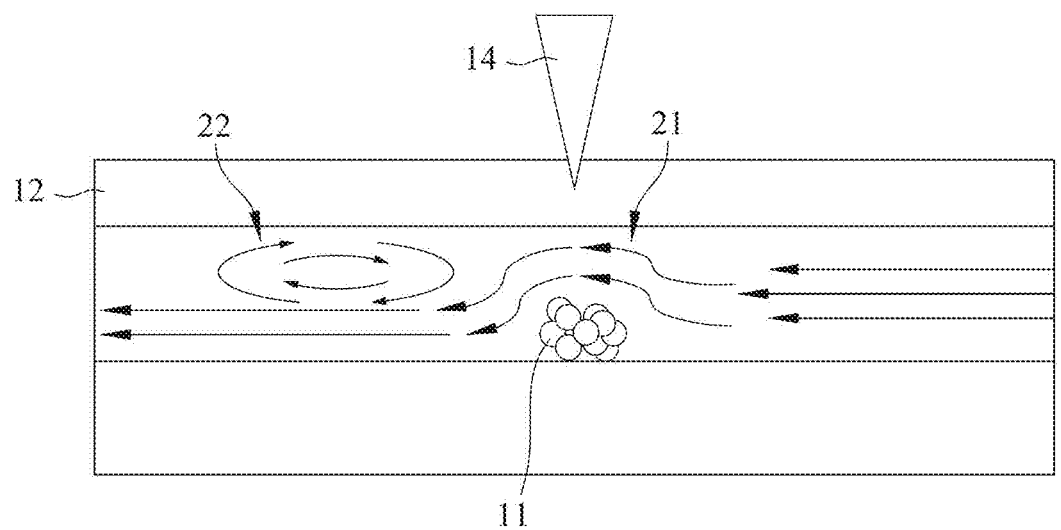
FIG. 2b is a schematic diagram showing the blood flow changes while the MBs aggregate.

Flowing MBs 11 in blood vessels 12 is shown in FIG. 2a. While we transmit focused ultrasound pulses using an ultrasound transducer 14, the MBs 11 aggregated and disturbed the blood flow, such as flow velocity changes (the arrow 21) and downstream vortex (the arrow 22) produces, as shown in FIG. 2b.

Thus, we provides a method of detecting microbubbles in a vessel of an affected part, comprising: delivering an ultrasonic energy within the affected part to aggregate the microbubbles to form a plurality of aggregated microbubbles; acquiring a phase-contrast magnetic resonance image by a magnetic resonance device; and analyzing the phase-contrast magnetic resonance image to obtain a velocity value of each pixel of a region of interest in the phase-contrast magnetic resonance image, wherein the plurality of aggregated microbubbles is located at a pixel that the velocity value is within the lowest 10%.

In an embodiment of the present invention, further comprising: analyzing the phase-contrast magnetic resonance image to obtain a vorticity value of each pixel of the region of interest; wherein the plurality of aggregated microbubbles is located at a pixel that the velocity value is within the lowest 10% and the vorticity value is −0.18 to 0.18.

In the embodiments of the present invention, the phase-contrast magnetic resonance image is a plurality of phase-contrast magnetic resonance images in a time sequence.

In the embodiments of the present invention, the method described above further comprising: calculating a velocity change of each pixel of the region of interest in the plurality of phase-contrast magnetic resonance images, the velocity change is defined as follows:

$$\text{Velocity change (\%)} = \frac{\text{velocity} - \text{average velocity during } preFUS}{\text{average velocity during } preFUS} \times 100\%,$$

wherein preFUS is a time duration before the ultrasonic energy delivered; and a concentration of the microbubbles is equal to (the velocity change−A)/B, wherein A is 1 to 1.5 and B is 7.56 to 11.34.

In the embodiments of the present invention, the method described above further comprising: calculating a temporal velocity standard deviation of each pixel of the region of interest in the plurality of phase-contrast magnetic resonance images; and a concentration of the microbubbles is equal to the temporal velocity standard deviation/C, wherein C is 0.04 to 0.06.

In the embodiments of the present invention, the method described above further comprising: calculating a temporal velocity standard deviation of each pixel of the region of interest in the plurality of phase-contrast magnetic resonance images; and calculating a range of temporal velocity standard deviation which is 90th percentile of the temporal velocity standard deviation minus 10th percentile of temporal velocity standard deviation, wherein a concentration of the microbubbles is equal to (the range of the temporal velocity standard deviation−D)/E, wherein D is 0.0136 to 0.0204 and E is 0.0856 to 0.1284.

In an embodiment of the present invention, the microbubbles have a diameter of 1-1.5 μm and were substantially composed of $C_3F_8$ gas or $C_5F_{12}$ droplet core encapsulated by a lipid shell.

Figure 3A:
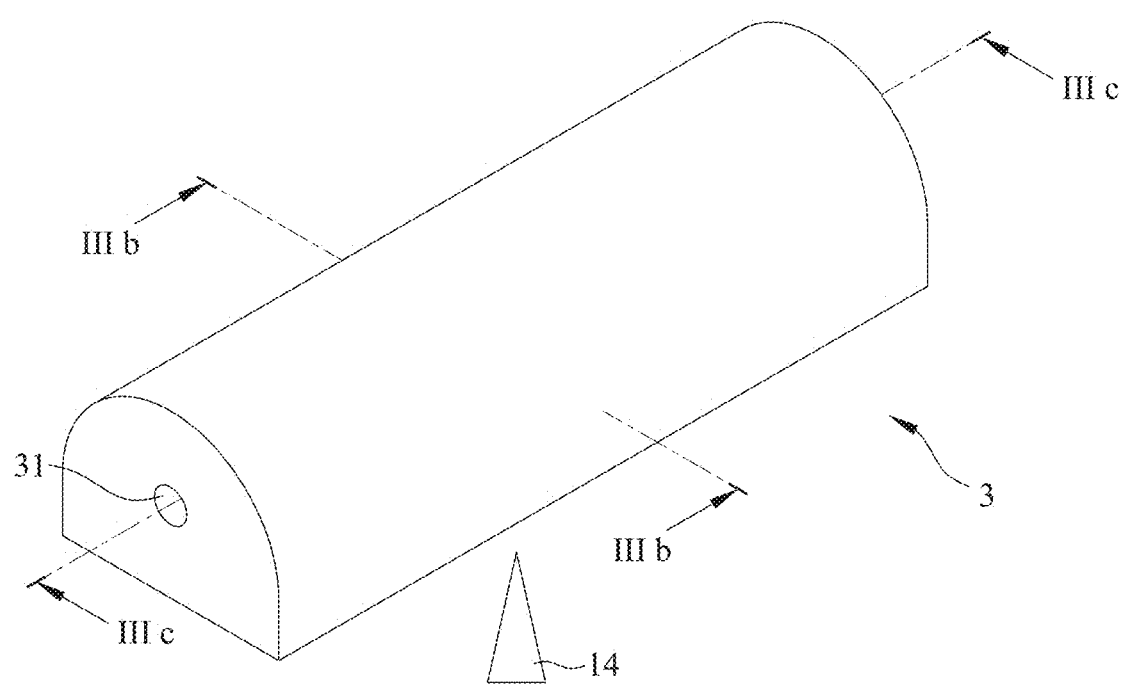
FIG. 3a is a schematic diagram showing the phantom used in the embodiment.
Figure 3B:
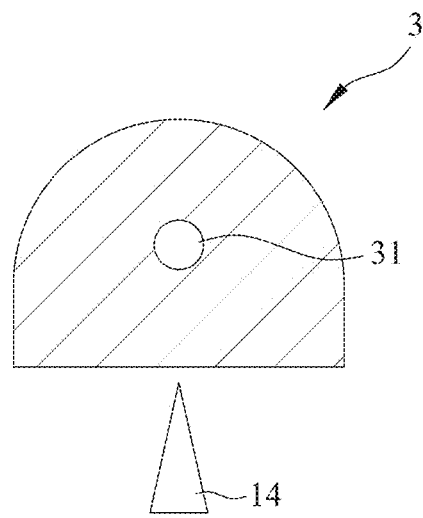
FIG. 3b is a sectional view taken along the IIIb-IIIb line in FIG. 3a (a schematic diagram showing the axial plane of the phantom)
Figure 3C:
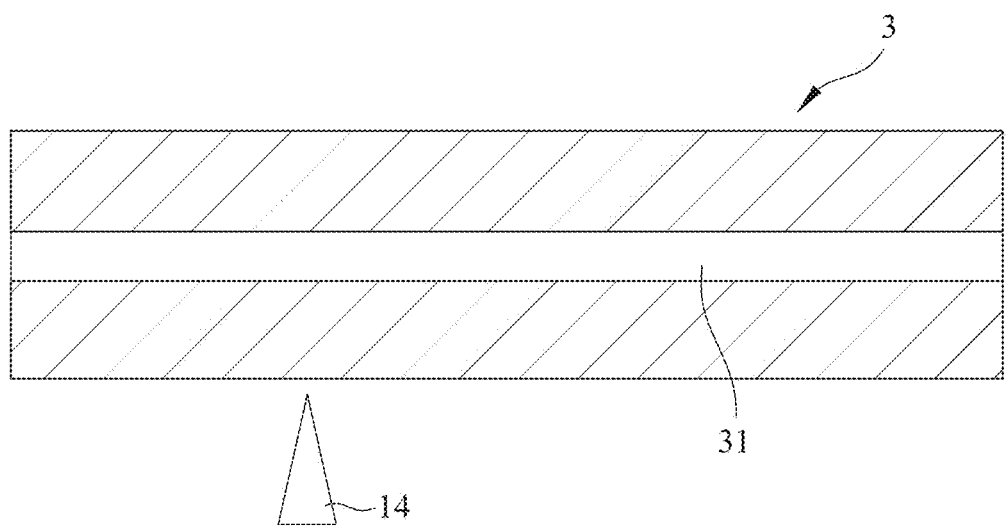
FIG. 3c is a sectional view taken along the IIIc-IIIc line in FIG. 3a (a schematic diagram showing the sagittal plane of the phantom)

We adopted phase-contrast MRI (PC-MRI) to real-time acquire flow velocity information with transmitting focus ultrasound (FUS) pulses (the secondary radiation force) on MBs in a flowing phantom. The phantom 3 is shown in FIG. 3a. The phantom has a semi-cylindrical shape and a hollow chamber 31 passing through. The hollow chamber 31 fulfills a fluid and the MBs 11 distribute in the fluid. In the embodiments of the specification, the imaging planes of PC-MRI as shown in FIG. 3b (axial plane) and FIG. 3c (sagittal plane). We aim to locate the positions of aggregated MBs.

MBs were diluted to the concentration of 0.1, 0.2, 0.5, and 1% (v/v). The solutions of MBs (lipid shell with $C_3F_8$, mean diameter=1.25 μm (Number %)) were injected with a velocity of 1 cm/s into the gel phantom with 6-mm hollow chamber. Continuous FUS pulses were transmitted by a single-element probe (central frequency 1.041 MHz, 2.5 cm diameter, 2.0 cm curvature, RK300, FUS Instruments, Toronto, Canada) to MBs solutions with acoustic pressure of 100 kPa. All images were acquired with PC-MRI (TR/TE=26.9/8.4 ms, pixel size=0.3×0.3 mm, pixel bandwidth=260 Hz/pixel, flip angle=10°, Venc=6 cm/s, temporal resolution=2.2 s) in a 7 Tesla scanner (ClinScan, Bruker, Germany). The imaging slices were selected in a transverse view of the chamber. We acquired 30 measurements (Pre-FUS=1-9, FUS=10-20, Post-FUS=21-30). A self-developed analyzing program was written in Matlab. The regions-of-interest were determined in magnitude images and transferring to phase images for analyzing the flow velocity information.

For the axial images of PC-MRI, we found the flow velocity of the fluid increases during FUS transmission and larger velocity can be observed with increased MBs concentrations. We calculated the pixel-wise velocity change and temporal standard deviation (STD) of velocity to evaluate the influence of the formation of bubbles. The velocity change is defined as follows:

$$\text{Velocity change (\%)} = \frac{\text{velocity} - \text{average velocity during } preFUS}{\text{average velocity during } preFUS} \times 100\%,$$

wherein preFUS is a time duration before the ultrasonic energy delivered.

The temporal standard deviation is defined as follows:

$$\text{Temporal } STD = \sqrt{\frac{\sum_{i=1}^{\# \text{ of meas.}} (velocity_i - \text{mean velocity})^2}{\# \text{ of meas.}}},$$

wherein # of meas. is a number of measurements.

Figure 4:
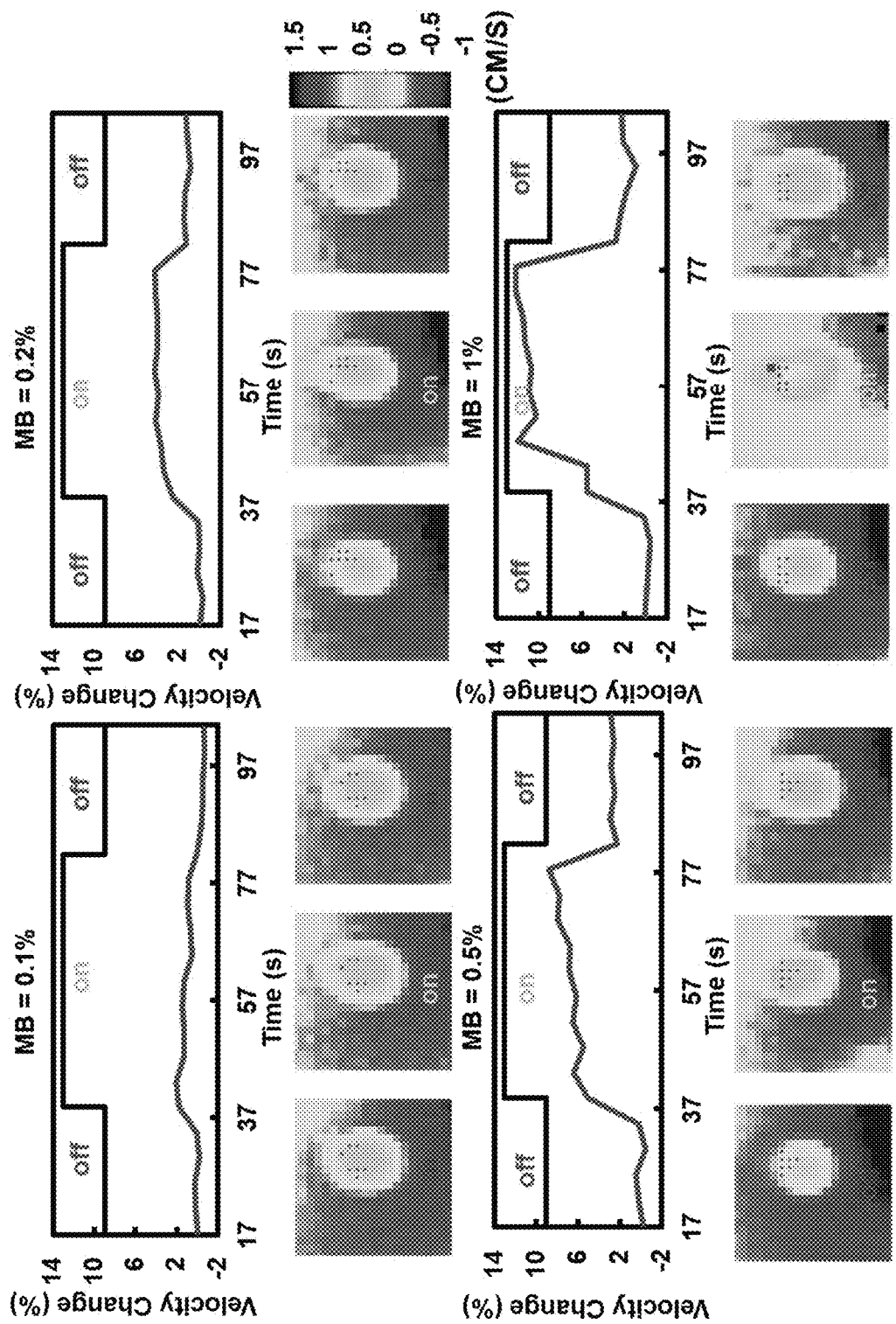
FIG. 4 shows the pixels with top 90% standard deviation (STD) were defined as regions with influence of the formation of aggregated microbubbles in different MBs concentrations.

The pixels with top 90% of velocity change were defined as the region with velocity change due to the aggregated bubbles (FIG. 4). The dots in each PC-MRI axial images in FIG. 4 represent the top 90% velocity STD.

Figure 5:
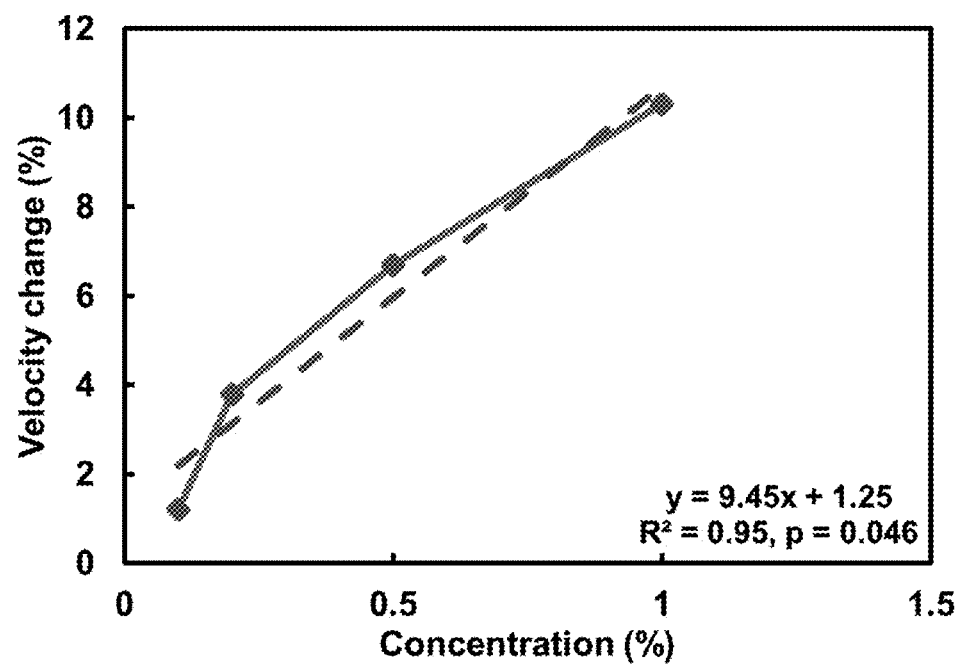
FIG. 5 shows the correlations of % velocity change with MBs concentration; the relationship between % velocity change of vertical axis and MBs concentration of horizontal axis is % velocity change=9.45×MBs concentration+1.25.

As shown as FIG. 5, velocity change (%) presented high positive correlation ($R^2$=0.95, p=0.046) with MBs concentrations, showing the velocity changes are highly proportional to the MBs concentrations. The relationship between velocity change (%) of vertical axis and MBs concentration of horizontal axis is velocity change (%)=9.45×MBs concentration+1.25.

Figure 6:
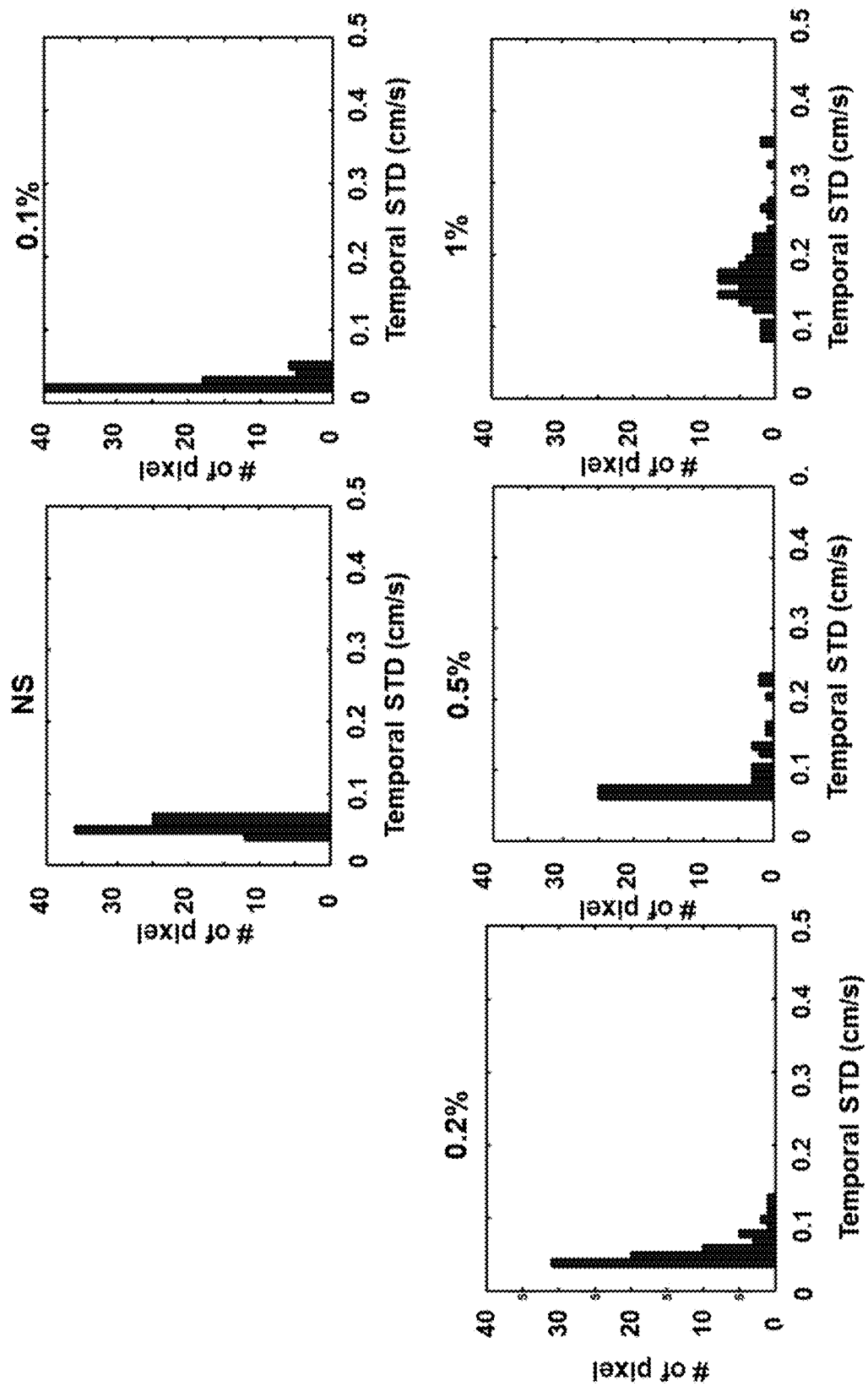
FIG. 6 shows the histograms of temporal STD with MBs concentration of 0.1%, 0.2%, 0.5%, and 1%; NS: normal saline (blank group)
Figure 7:
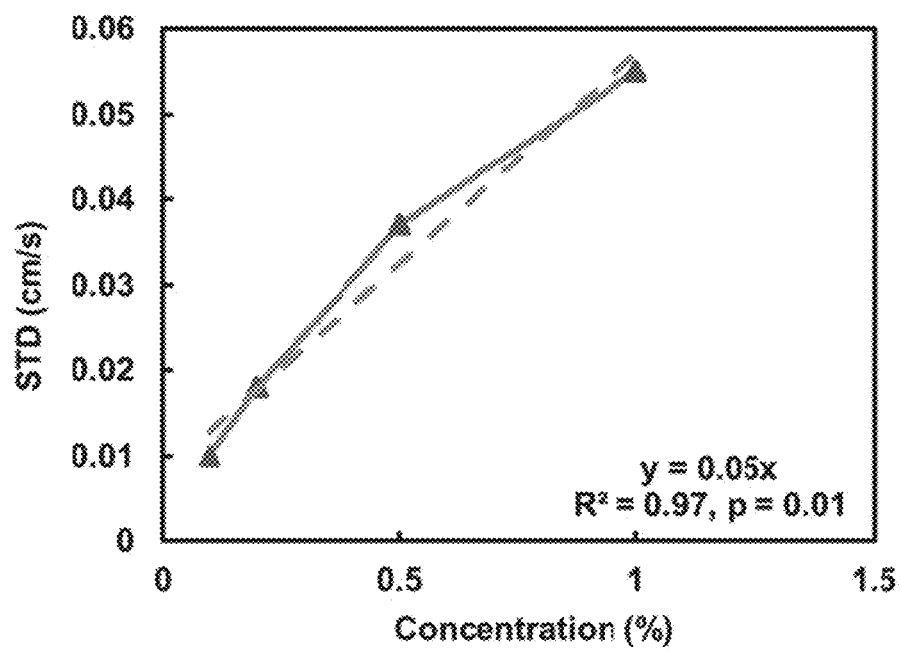
FIG. 7 shows the correlations of temporal STD of velocity with MBs concentration; the relationship between temporal STD of velocity of vertical axis and MBs concentration horizontal axis is temporal STD of velocity=0.05×MBs concentration.

The histograms shown in FIG. 6 demonstrated that the maximum of STD increased with the increase of MBs concentrations. FIG. 7 displayed high correlation between temporal STD ($R^2$=0.97, p=0.01) and MBs concentrations, indicating that FUS can induce more fluctuating flow velocity in MBs with higher concentrations. The relationship between temporal STD of velocity of vertical axis and MBs concentration horizontal axis is temporal STD of velocity=0.05×MBs concentration.

Figure 8:
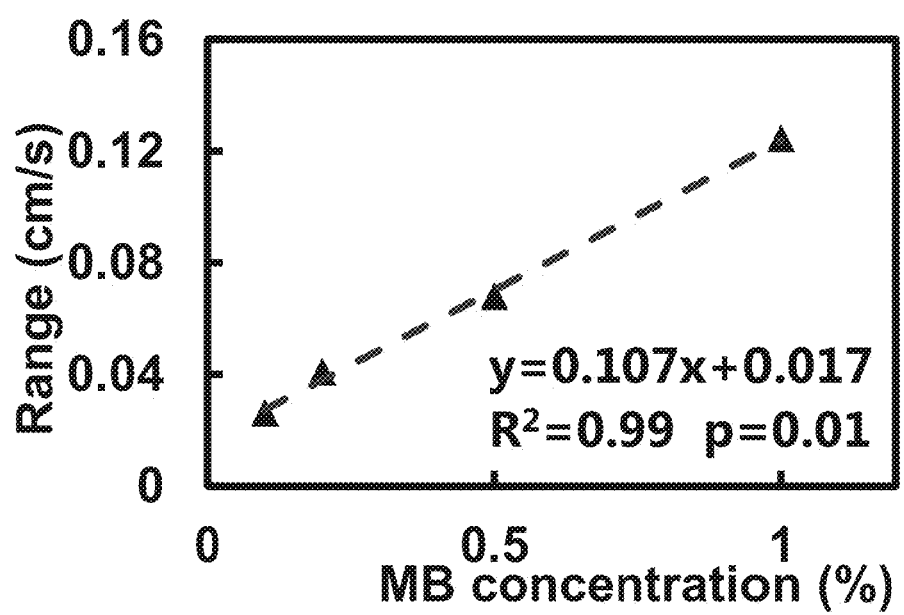
FIG. 8 shows the correlations of the range of temporal velocity STD with MBs concentration; the relationship between the range of temporal velocity STD of vertical axis and MBs concentration horizontal axis is the range of temporal velocity STD=0.107×MBs concentration+0.017.

Then, we calculated the range of temporal velocity STD, which defined as 90th percentile of the temporal velocity STD minus 10th percentile of temporal velocity STD in temporal STD mapping. As shown as FIG. 8, the range of velocity temporal STD reveals high positive correlation ($R^2$=0.99, p=0.01) with MBs concentrations. The relationship between the range of temporal velocity STD of vertical axis and MBs concentration horizontal axis is the range of temporal velocity STD=0.107×MBs concentration+0.017.

For the sagittal images of PC-MRI, we observed vector field of the images and calculated vorticity for each pixel of the images. The vorticity is defined as follows:

$$\frac{D\omega}{Dt} = \frac{\partial \omega}{\partial t} + (u \cdot \nabla)\omega$$

Figure 9:
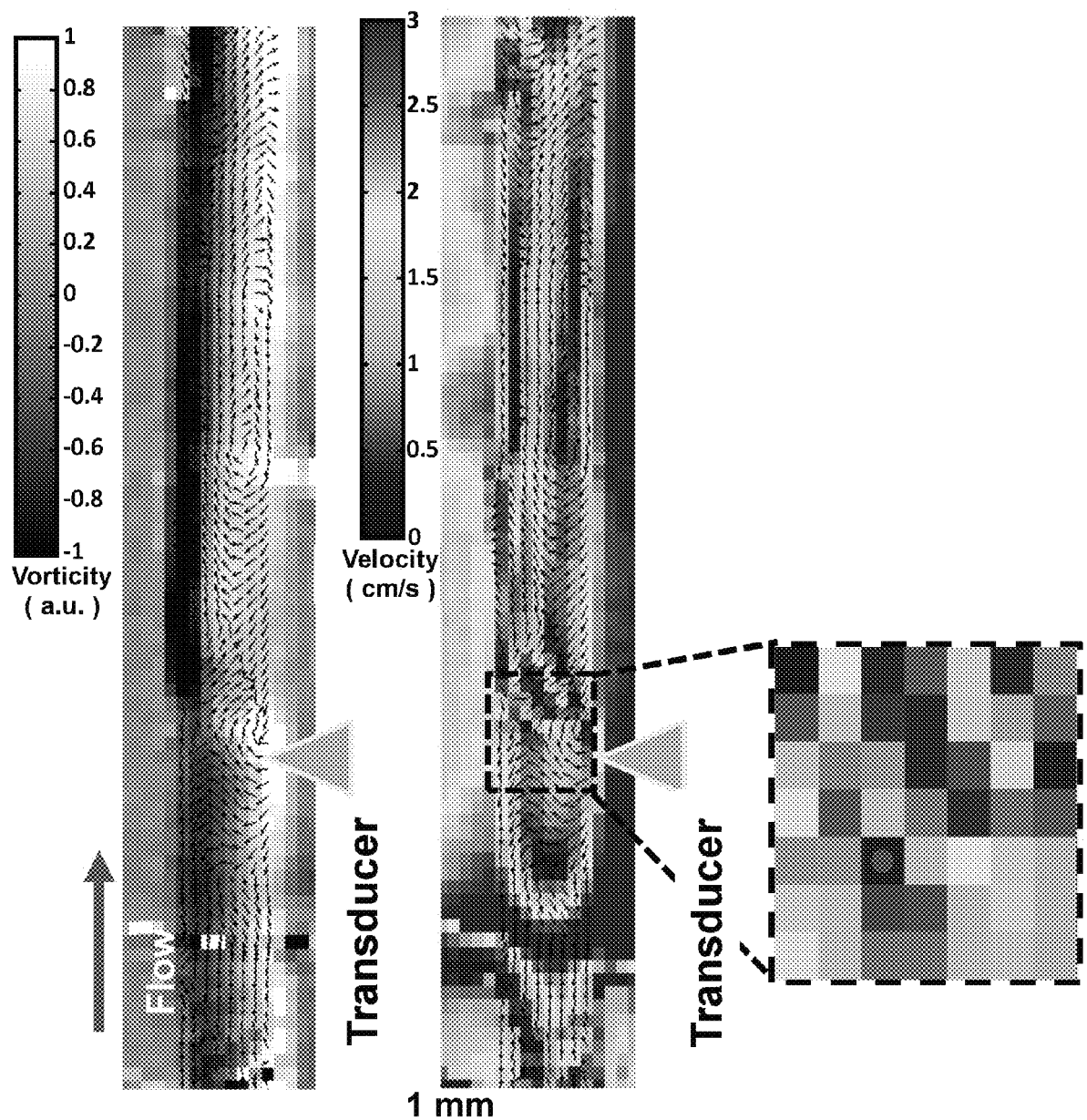
FIG. 9 shows according to the velocity and the vorticity conditions, the aggregated microbubbles were localized at the pixel with a red dot.

In the vector view of the images, we found more disturbed flow increased with MBs concentrations. Further, higher vorticity appeared near the chamber wall and vortex area expanded while FUS was applying. According to both of the position (by magnitude image) and the depth (2 cm) of the transducer, aggregated microbubbles was localized at pixels with the lowest 10% of velocity and vorticity approximately 0 (−0.15–0.15). According the velocity and the vorticity conditions, the aggregated microbubbles was at the pixel with a red dot, as shown in FIG. 9.

We used PC-MRI to real-time evaluate the velocity, vorticity, temporal STD of velocity and % velocity change in a chamber with flowing MBs. We observed that the aggregated microbubbles was localized at pixels with the lowest 10% of velocity and vorticity approximately 0 (−0.15–0.15), and the % velocity change, the temporal STD of velocity as well as the range of velocity temporal STD increased with increasing MBs concentrations. This finding can be attributed to the increased aggregated bubbles size and thus more substantial disturbance of local flow. The % velocity change increased from pre-FUS to FUS_early (a time duration that FUS just delivered) was resulted from the formation of aggregated bubbles, which can narrow the chamber diameter and accordingly lead to higher flow velocity.

Furthermore, the acoustic pressure of 0.025, 0.05, and 0.075 MPa are also tested according to the experiment described above. The MBs detecting results are similar with the result that employed acoustic pressures of 0.1 MPa.

In conclusion, we verified the feasibility of using PC-MRI to evaluate the temporal STD of velocity and % velocity change in a chamber with flowing MBs. By calculating the velocity, vorticity, temporal STD of velocity and % velocity change, it is helpful to identify the size and location of aggregated bubbles and further obtain the amount of MBs near the region we interested in. Thus, we can detect or monitor the drug dose near a target location (such as a tumor site) by evaluating the size, location and concentration of drug-loaded MBs.

The preferred embodiments described above are disclosed for illustrative purpose but not for limiting the modifications and variations of the present invention. Thus, any modifications and variations made without departing from the spirit and scope of the invention should still be covered by the scope of this invention as disclosed in the accompanying claims.

What is claimed is:

1. A method of detecting microbubbles in a vessel of an affected part, comprising:
    delivering an ultrasonic energy within the affected part to aggregate the microbubbles to form a plurality of aggregated microbubbles;
    acquiring a phase-contrast magnetic resonance image by a magnetic resonance device; and
    locating the plurality of aggregated microbubbles by analyzing the phase-contrast magnetic resonance image to obtain a velocity value and a vorticity value of fluid flow in a region of interest in the phase-contrast magnetic resonance image;
    wherein the plurality of aggregated microbubbles is located at wherein the velocity value is within the lowest 10%, and the vorticity value is −0.18 to 0.18;
    wherein the ultrasonic energy has a frequency of 0.83-1.25 MHz and an acoustic pressure of 0.025-0.1 MPa; and
    wherein the region of interest is an area of the vessel.

2. The method as claimed in claim 1, wherein the region of interest is an area of the vessel.

3. The method as claimed in claim 1, wherein the microbubbles have a diameter of 1-1.5 µm.

4. The method as claimed in claim 1, wherein the microbubbles were substantially composed of $C_3F_8$ gas or $C_5F_{12}$ droplet core encapsulated by a lipid shell.

5. The method as claimed in claim 4, wherein the microbubbles further comprise a drug for treating the affected part.

6. The method as claimed in claim 1, wherein the phase-contrast magnetic resonance image is a plurality of phase-contrast magnetic resonance images in a time sequence.

7. The method as claimed in claim 6, further comprising:
    calculating a velocity change of each pixel of the region of interest in the plurality of phase-contrast magnetic resonance images, the velocity change is defined as follows:

$$\text{Velocity change (\%)} = \frac{\text{velocity} - \text{average velocity during } preFUS}{\text{average velocity during } preFUS} \times 100\%,$$

wherein preFUS is a time duration before the ultrasonic energy delivered, and a concentration of the microbubbles is equal to (the velocity change a first y-intercept value)/a first slope value, wherein the first y-intercept value is 1 to 1.5 and B the first slope value is 7.56 to 11.34.

8. The method as claimed in claim 7, wherein the first y-intercept value is 1.25 and the first slope value is 9.45.

9. The method as claimed in claim 6, further comprising:
    calculating a temporal velocity standard deviation of each pixel of the region of interest in the plurality of phase-contrast magnetic resonance images,
    wherein a concentration of the microbubbles is equal to the temporal velocity standard deviation/a second slope value, wherein the second slope value is 0.04 to 0.06.

10. The method as claimed in claim 9, wherein the second slope value is 0.05.

11. The method as claimed in claim 6, further comprising:
    calculating a temporal velocity standard deviation of each pixel of the region of interest in the plurality of phase-contrast magnetic resonance images; and
    calculating a range of temporal velocity standard deviation which is 90th percentile of the temporal velocity standard deviation minus 10th percentile of temporal velocity standard deviation,
    wherein a concentration of the microbubbles is equal to (the range of temporal velocity standard deviation a second y-intercept value)/a third slope value, and the second y-intercept value is 0.0136 to 0.0204 and the third slope value is 0.0856 to 0.1284.

12. The method as claimed in claim 11, wherein the second y-intercept value is 0.017 and the third slope value is 0.107.

* * * * *